(12) United States Patent
Muller-Feuga et al.

(10) Patent No.: US 6,815,204 B2
(45) Date of Patent: Nov. 9, 2004

(54) METHOD FOR IMPROVING TRANSFER IN A BIOLOGICAL REACTION CHAMBER

(75) Inventors: Arnaud Muller-Feuga, Soreze (FR); Jack Legrand, Saint-Nazaire (FR); Jérémy Pruvost, Saint-Reverend (FR); Patrick Legentilhomme, Dreffeac (FR); Roland Leguedes, L'Hopital-Camfrout (FR)

(73) Assignee: Institut Francais de Recherche pour l'Exploitation de la Mer (IFREMER), Issy les Moulineaux (FR)

( * ) Notice: Subject to any disclaimer, the term of this patent is extended or adjusted under 35 U.S.C. 154(b) by 135 days.

(21) Appl. No.: 10/312,792

(22) PCT Filed: Jul. 3, 2001

(86) PCT No.: PCT/FR01/02123
§ 371 (c)(1),
(2), (4) Date: Dec. 31, 2002

(87) PCT Pub. No.: WO02/02734
PCT Pub. Date: Jan. 10, 2002

(65) Prior Publication Data
US 2003/0170884 A1 Sep. 11, 2003

(30) Foreign Application Priority Data
Jul. 3, 2000 (FR) .............................................. 00 08587

(51) Int. Cl.[7] .................................................. C12N 5/00
(52) U.S. Cl. ...................... 435/393; 435/394; 435/420; 435/286.7
(58) Field of Search .................................. 435/383, 393, 435/394, 420, 260, 286.7, 292.1, 293.1

(56) References Cited

U.S. PATENT DOCUMENTS

| 5,939,313 A | * | 8/1999 | Cheng ...................... 435/289.1 |
| 5,958,761 A | * | 9/1999 | Yogev et al. ............. 435/292.1 |
| 6,509,188 B1 | * | 1/2003 | Trosch et al. ............. 435/292.1 |

FOREIGN PATENT DOCUMENTS

| EP | 0900766 | * | 3/1999 |
| FR | 2762326 | | 10/1988 |
| GB | 1509630 | * | 5/1978 |
| WO | WO/9603494 | * | 2/1996 |

* cited by examiner

Primary Examiner—David A. Redding
(74) Attorney, Agent, or Firm—Cohen, Pontani, Lieberman & Pavane

(57) ABSTRACT

The invention relates to a method of improving the transfer in an annular biological reaction chamber defined by coaxial inner and outer walls (11, 12) and in which there flows a liquid reaction medium containing a culture of microorganisms or of cells from vegetable or animal macroorganisms in suspension. At least one of the walls is an exchange wall enabling gaseous or liquid matter to be transferred or allowing light to pass through. The reaction medium is subjected to a turbulent primary flow that is helical and that under the action of centrifugal force creates rotary secondary vortices so as to encourage renewal of the culture in the vicinity of the exchange wall.

4 Claims, 2 Drawing Sheets

METHOD FOR IMPROVING TRANSFER IN A BIOLOGICAL REACTION CHAMBER

PRIORITY CLAIM

This is a U.S. national stage of application No. PCT/FR01/02123, filed on 03 Jul. 2001. Priority is claimed on that application and on the following application(s): Country: France, Application No.: 00/08587, Filed: 03 Jul. 2000.

BACKGROUND OF THE INVENTION

The invention relates to the field of using a liquid reaction medium for culturing microorganisms or isolated cells of vegetable or animal macroorganisms.

More precisely, the invention relates to a method of improving the yield of a biological reactor comprising at least one annular biological reaction chamber defined by two coaxial cylindrical walls, at least one of which is an exchange wall allowing gaseous or liquid matter to be transferred or allowing light to pass, and in which there flows axially a liquid reaction medium containing a culture of microorganisms or of isolated cells of vegetable or animal microorganisms in suspension, in which method the culture is subjected to a biosynthesis reaction activated by the matter or the light passing through said exchange wall.

The invention relates both to culturing phototrophic microorganisms or isolated cells, and to culturing heterotrophic microorganisms or isolated cells.

When culturing phototrophic microorganisms, visible light radiation and carbon dioxide gas are supplied, and the gas is consumed during the photosynthesis reaction with oxygen being produced. The oxygen must be removed since it is toxic above a certain concentration.

When culturing heterotrophic microorganisms, oxygen is supplied. The oxygen is consumed and carbon dioxide gas is produced which must be eliminated since it is toxic above a certain concentration.

FR A 2 762 326 describes a photobioreactor for culturing photoautotrophic microorganisms, the reactor comprising a plurality of horizontal annular chambers having a transparent inside wall surrounding a light chamber. The reaction medium is introduced axially into the annular chamber where it is subjected to turbulent movement.

When a liquid is introduced axially into an annular chamber, the molecules always remain at substantially the same distance from the axis of the chamber. If the movement is turbulent, then the molecules are moved short distances radially about a mean position. It can be deduced that the culture situated in the vicinity of the inside wall is strongly illuminated, whereas the culture located close to the outside wall is poorly illuminated. Very strong turbulence might perhaps lead to the culture in the vicinity of the inside wall being renewed. However microorganisms are sensitive to shear, and high levels of turbulence are harmful for production.

In FR A 2 762 326, the absorbance of the culture is controlled by adding transparent or reflecting particles to the reaction medium, said particles being of a density that is substantially equal to that of the reaction medium, with the volume percentage of the particles in the reaction medium being a function of the species of microorganism being cultivated, of the thickness of the chamber, and of the desired final concentration of the culture in the reaction medium.

That disposition makes it possible to ensure that all of the microorganisms are illuminated throughout their transfer in the annular chamber, and regardless of the type of microorganism. However, it does not enable growth to be continued in darkness after the microorganisms have been illuminated for a duration $T_{lum}$.

SUMMARY OF THE INVENTION

The object of the invention is to improve the yield of that type of photobioreactor by creating a flow in the chamber that encourages renewal of the culture in the vicinity of the illuminated wall so that microorganisms that have been illuminated continue their growth when they enter into non-illuminated zones.

Thus, for a given flow rate of the reaction medium, microorganism growth is greater than that obtained by the known method.

The method of the invention is equally applicable to isolated cells or microorganisms other than phototrophic microorganisms.

In particular, when the biological reaction is obtained by consuming a gas (carbon dioxide gas or oxygen), and producing another gas for elimination (oxygen or carbon dioxide gas), the inside wall of the biological reaction chamber may be constituted by a hydrophobic semipermeable membrane which retains the reaction medium inside the chamber while allowing one of the gases to pass through. When feeding a gas, the gas is under pressure in the inside tube of the chamber (source), and eliminating a gas, the inside chamber (well) is under suction.

It should be observed that the gas exchange wall may be the outside wall of the biological reaction chamber, in which case the chamber is placed in a duct of larger diameter than is used for delivering a gas, preferably under pressure (source). Both walls of the biological reaction chamber may be semipermeable and hydrophobic, with the inside wall forming a well under suction for eliminating the toxic gas and with the outside wall being connected to a source of the gas to be consumed during the biological reaction. Similarly, one of the walls may be transparent to enable the culture to be illuminated while the other wall may be semipermeable and preferably hydrophobic to enable a gas to be delivered or a toxic gas to be eliminated after being produced during the photobioreaction.

When the biological reaction requires an organic or inorganic nutrient solution to be supplied, the inside wall of the biological reaction chamber is constituted by a hydrophilic porous membrane and defines a source of nutrient solution under pressure.

The method of the invention is characterized by the fact that the reaction medium flowing in said biological reaction chamber is subjected to a primary turbulent flow that is helical about the axis of the chamber, which flow under the action of centrifugal force generates rotary secondary vortices, thereby encouraging the culture to be renewed in the vicinity of the exchange wall.

Advantageously, the reaction medium is subjected to a helical turbulent primary flow by introducing the reaction medium at one of the ends of the biological reaction chamber in a direction that is substantially perpendicular to the axis of the chamber and that is offset away from said axis.

Preferably, the reaction medium is introduced into the biological reaction chamber by means of a duct having an axis that is substantially perpendicular to the axis of the chamber, and that is connected tangentially to the outer wall of said chamber.

The internal transverse dimension of the duct in the direction perpendicular to the axis of the biological reaction chamber is no greater than the radial thickness of said chamber.

BRIEF DESCRIPTION OF THE DRAWINGS

Other advantages and characteristics of the invention appear on reading the following description made by way of example and with reference to the accompanying drawings, in which.

DETAILED DESCRIPTION OF THE PRESENTLY PREFERRED EMBODIMENTS

Figure 1:
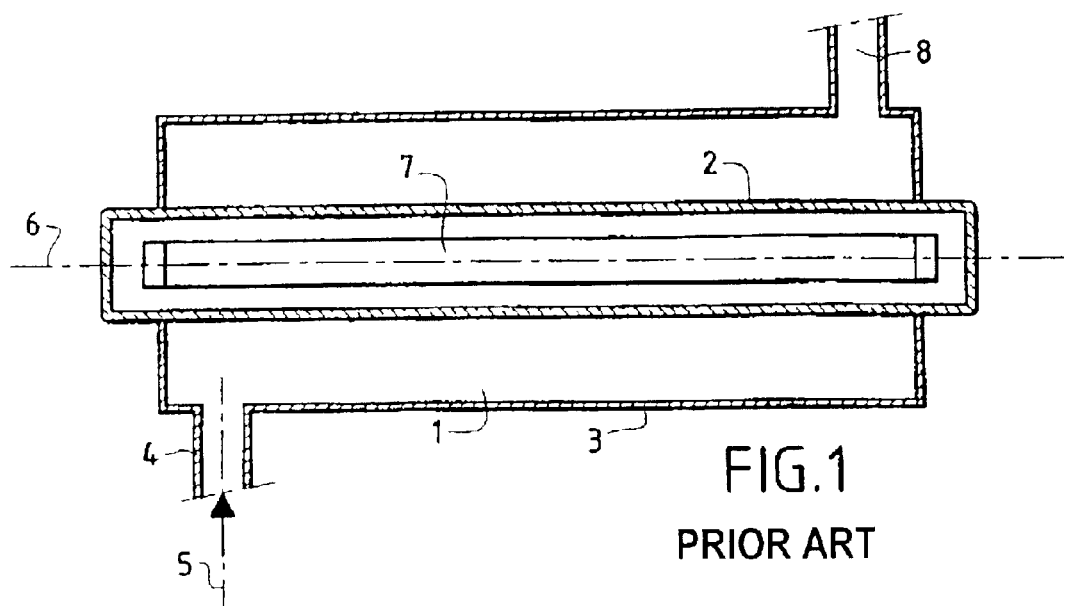
FIG. 1 shows an annular chamber of a prior art photobioreactor.

FIG. 1 shows a chamber 1 of a photobioreactor in accordance with FR A 2 762 326. That annular chamber is defined on the inside by a transparent cylindrical wall 2, and on the outside by a second transparent cylindrical wall 3. The liquid reaction medium is introduced at one end of the chamber 1 via an inlet duct 4 whose axis 5 lies in a plane containing the axis 6 of the chamber 1. A light-emitting tube 7 is placed on the axis 6 of the transparent wall 2. The length of the chamber 1 is substantially equal to 1500 millimeters (mm) and its thickness is close to 30 mm. The reaction medium flows axially inside the chamber 1 in turbulent manner and it is removed via an outlet duct 8 disposed at the end of the chamber 1 opposite from the inlet duct 4.

Figure 2:
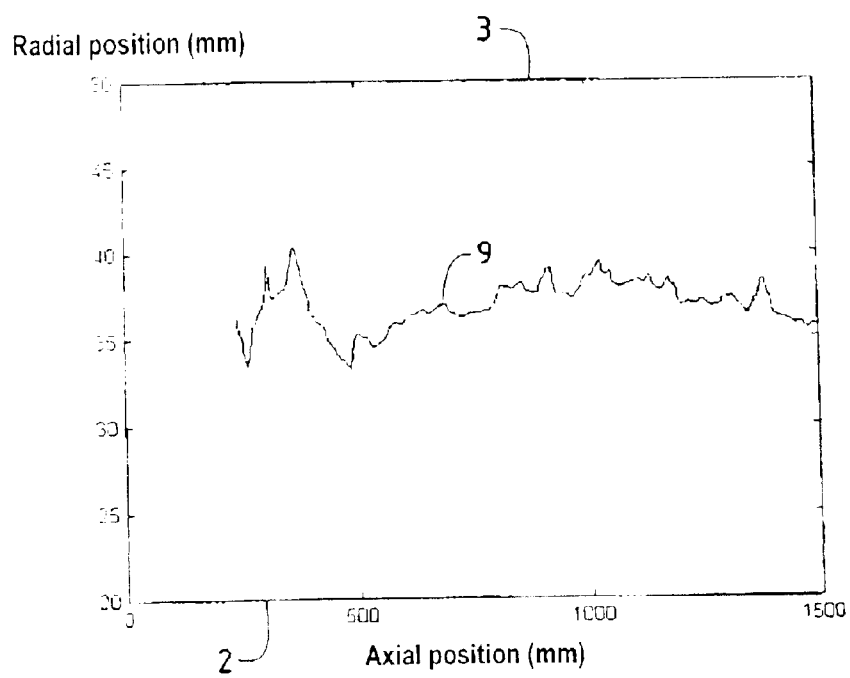
FIG. 2 is a graph showing the radial displacements of microorganisms in a prior art annular chamber into which the reaction medium enters in an axial direction lying in the plane of symmetry of the chamber.

The graph of FIG. 2 shows the radius of the trajectory 9 of a microorganism in the chamber 1. The path followed by this microorganism is subject to small radial displacements as it moves axially along the chamber 1. As a result there is no renewal of the culture in the vicinity of the transparent wall 2.

Figure 3:
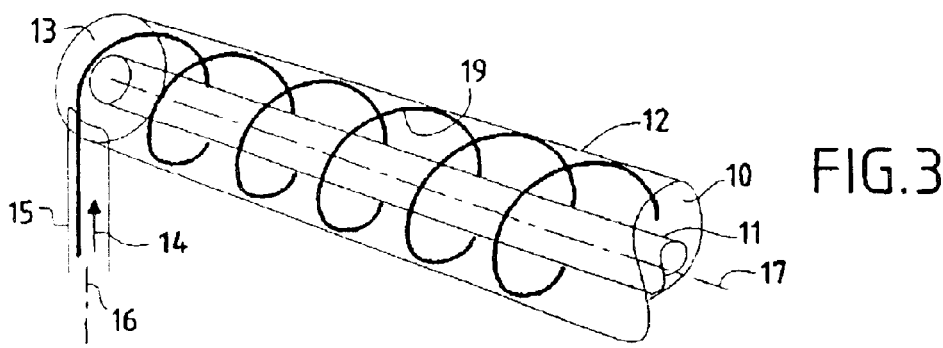
FIG. 3 is a diagram of a biological reaction chamber of the invention together with the duct for feeding the reaction medium.
Figure 4:
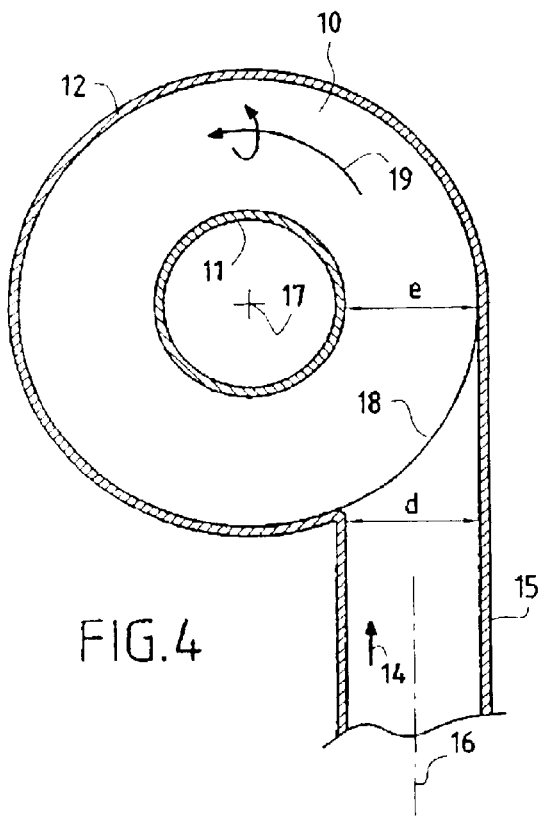
FIG. 4 is a radial section through the biological reaction chamber on a plane containing the axis of the duct for feeding the reaction medium.
Figure 5:
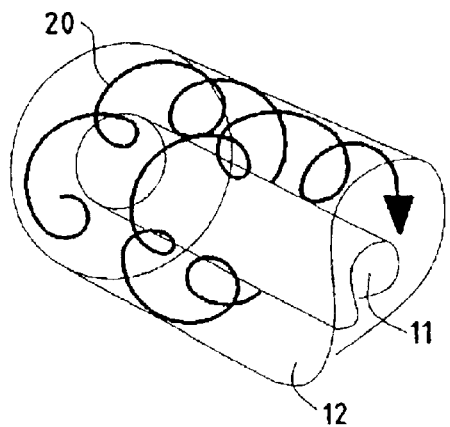
FIG. 5 is a diagram showing the creation of secondary rotary vortices.

FIGS. 3 and 4 show a biological reaction chamber 10 of the annular type defined by an inner cylindrical wall 11 and an outer cylindrical wall 12 interconnected at their end by at least one end wall 13. The inner wall 11 and the outer wall 12 are coaxial, and at least the inner wall 11, referred to as the "exchange" wall, enables a gaseous or liquid material to pass through or allows light to pass through as is needed for biological reaction by microorganisms or by isolated cells of vegetable or animal macroorganisms in suspension in the reaction medium 14, which liquid flows inside the annular chamber 10. The reaction medium 14 is inserted at the end of the chamber 10 close to its end wall 13 by means of a duct 15 whose axis 16 is perpendicular to the axis 17 of the chamber 10 and is offset away from said axis 17. The feed duct 15 is connected tangentially to the outer wall 12 of the chamber 10. In other words, the duct 15 presents a generator line remote from the axis 17 of the chamber 10 which is tangential to the outside wall 12. The section of the feed duct 15 is circular or curvilinear, but its dimension d in the direction perpendicular to the axis 17 of the chamber 10 is no greater than the radial gap e between the inner and outer walls 11 and 12 of the chamber 10. The cylinder of the orifice 18 of the feed duct 15 therefore does not present any intersection with the inner cylindrical wall 10.

The flow of liquid reaction medium delivered by the feed duct 15 thus penetrates tangentially and substantially perpendicularly to the axis 17 at one of the ends of the annular chamber 10. Because the feed duct 15 is situated in the immediate vicinity of the end wall 13, the reaction medium 14 flows inside the chamber 10 along a primary turbulent path that is helical around the axis 17 of the chamber 10. The helical axis of this primary turbulent flow is referenced 19 in FIG. 3. In addition, because of centrifugal forces, the primary movement generates secondary vortices 20 that rotate about the helical axis of the primary vortex. The turbulent flow 20 as obtained in this way is not sustained, so it tends to attenuate by reducing its circumferential speed. Nevertheless it remains active over a distance of at least 1500 mm.

The axis 16 of the feed duct 15 is not necessarily rectilinear. What matters is that the reaction medium 14 penetrates into the chamber 11 along a direction that is off-center relative to the axis 17 and substantially perpendicular thereto and that the flow penetrates tangentially to the outer wall 12 to avoid shear and recirculation in the inlet zone.

The section of the inlet duct 15 is less than the cross-section of the chamber 10 so that the axial speed Va of the reaction medium in the chamber is less than its speed Vc in the feed duct. The speed factor Vc/Va can be equal to 4, for example, and may lie in a broad range, for example 2 to 10. This speed factor is selected so that there is a well-marked vortex 19 along the entire length of the chamber 10 and so that it is certain that the culture close to the inner wall 11 will be renewed.

Figure 6:
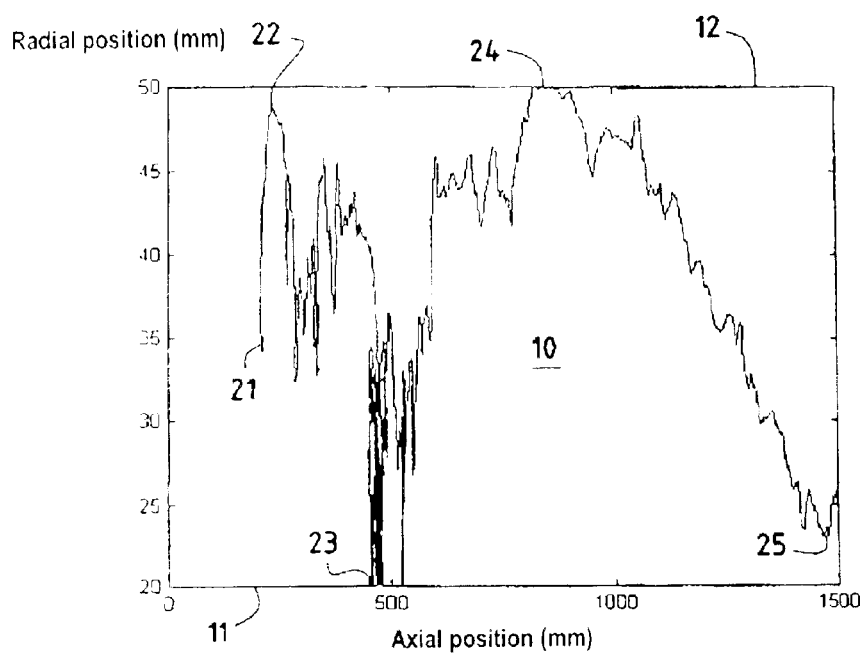
FIG. 6 is a graph showing the radial displacements of microorganisms within the biological reaction chamber of the invention.

FIG. 6 shows the radius of the trajectory of a microorganism within the chamber 10 when the reaction medium is introduced in the manner described above. It can be seen that starting from the middle entry point 21, the microorganism comes close to the outer wall 12 at a point 22 and then returns towards the inner wall 11 at a point 23, then returning again to the outer wall 12 at a point 24 and returning to the vicinity of the inner wall 11 at a point 25, close to the other end of the biological reaction chamber 10.

It should be observed that the specifications concerning the length of the inlet duct 15 are not constraining, turbulent primary flows have been obtained with ducts having a length of 12 mm. The specifications concerning the outlet orifice from the chamber 10 are not constraining. In particular it is not necessary for the outlet duct to be in a tangential position.

In the example described in detail above that applies to a photobioreactor, the inner wall 11 is transparent and passes light as emitted by a light source. The wall may be a hydrophobic semipermeable wall, and the cavity inside the inner wall 11 may contain carbon dioxide gas under pressure in order to nourish the microorganism or it may be put at reduced pressure in order to extract from the reaction medium the oxygen that is produced during the biological reaction, which oxygen is toxic above a certain concentration.

The wall 10 may be porous and hydrophilic. The inner cavity then serves as a source of nutrient solution under pressure for culturing heterotrophic or phototrophic microorganisms.

What is claimed is:

1. A method of improving the yield of a biological reactor comprising at least one annular biological reaction chamber (10) defined by two coaxial cylindrical walls (11, 12), at least one of which (11) is an exchange wall allowing gaseous or liquid matter to be transferred or allowing light to pass, and in which there flows axially a liquid reaction medium (14) containing a culture of microorganisms or of isolated cells of vegetable or animal microorganisms in suspension, in which method the culture is subjected to a biosynthesis reaction activated by the matter or the light passing through said exchange wall (11), the method being characterized by the fact that the reaction medium (14) flowing in said biological reaction chamber (10) is subjected to a primary turbulent flow (19) that is helical about the axis (17) of the chamber (10), which flow under the action of centrifugal force generates rotary secondary vortices (20), thereby encouraging the culture to be renewed in the vicinity of the exchange wall (11).

2. A method according to claim 1, characterized by the fact that the reaction medium (14) is subjected to a helical turbulent primary flow by introducing the reaction medium at one of the ends of the biological reaction chamber (10) in a direction that is substantially perpendicular to the axis (17) of the chamber and that is offset away from said axis (17).

3. A method according to claim 2, characterized by the fact that the reaction medium (14) is introduced into the biological reaction chamber (10) by means of a duct (15) having an axis (16) that is substantially perpendicular to the axis (17) of the chamber (10), and that is connected tangentially to the outer wall (12) of said chamber (10).

4. A method according to claim 3, characterized by the fact that the internal transverse dimension (d) of the duct (15) in the direction perpendicular to the axis (17) of the biological reaction chamber (10) is no greater than the radial thickness (e) of said chamber (10).

* * * * *